United States Patent [19]

Vatne et al.

[11] 4,015,014
[45] Mar. 29, 1977

[54] METHOD FOR THE USE OF ARYL AZINES AS ANTHELMINTICS

[75] Inventors: Robert D. Vatne; Paul B. Budde; Jack P. Arrington, all of Midland, Mich.

[73] Assignee: The Dow Chemical Company, Midland, Mich.

[22] Filed: Mar. 17, 1976

[21] Appl. No.: 667,779

[52] U.S. Cl. .................................. 424/324; 424/327
[51] Int. Cl.² ................ A61K 31/165; A61K 31/15
[58] Field of Search ........................... 424/327, 324

[56] References Cited

OTHER PUBLICATIONS

Schiller et al.–Chem. Abst. vol. 83 (1975) p. 120,832h.

*Primary Examiner*—Sam Rosen
*Attorney, Agent, or Firm*—S. Preston Jones; C. Kenneth Bjork

[57] ABSTRACT

Aryl Azines corresponding to the formula

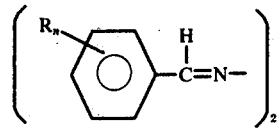

wherein R independently represents hydrogen, hydroxy, loweralkyl of 1 to 4 carbon atoms, loweralkoxy of 1 to 4 carbon atoms, alkylamino of 1 to 4 carbon atoms, acetamido or halo, and $n$ represents an integer of 1 or 2 are employed as anthelmintics for the control of gastrointestinal nematodes in animals and more specifically for the control of Haemonchus in ruminant animals.

28 Claims, No Drawings

METHOD FOR THE USE OF ARYL AZINES AS ANTHELMINTICS

BACKGROUND OF THE INVENTION

Helminthiasis, the infestation of an animal by certain species of parasitic worms, is one of the most common, serious and widespread animal diseases. Of special interest are those parasitic worms of the family Trichostrongylidae and the genus Haemonchus. These parasites have the common name of twisted stomach worm and cause the diseases in ruminants known as haemonchosis, stomach worm disease or wireworm disease. These worms have been found to invade the abomasum of sheep, cattle, goats, moose, deer, bison and a number of other ruminants.

The above parasites during their maturation and growth have a very deleterious effect upon the animal and its rate of growth. In the abomasum, the parasites erode the epithelial tissues bringing about hemorrhage, anemia, weakness and tissue necrosis. Animals if they do not succumb to gross parasitism, are rendered economically unfit by weakness, lower vitality and poor growth and reproduction. The economic loss to the cattle and sheep industry of the United States from gross parasitism is extremely high.

While many drugs have been developed to try and offset the effects of these diseases, they have not been completely satisfactory for a variety of reasons. In some cases the drugs have not been sufficiently effective, and in others the cost of the drug has been too high and in many cases the parasites have developed a resistance to the drug.

SUMMARY OF THE INVENTION

The present invention is directed to a method of controlling gastrointestinal nematodes in animals and more specifically controlling the nematode of the genus Haemonchus in sheep. The active anthelmintic agent is an aryl azine corresponding to the formula

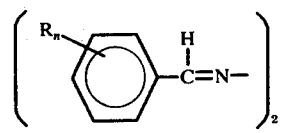

wherein R independently represents hydrogen, hydroxy, loweralkyl of 1 to 4 carbon atoms, loweralkoxy of 1 to 4 carbon atoms, alkylamino of 1 to 4 carbon atoms, acetamido or halo and $n$ represents an integer of 1 or 2.

The term "loweralkyl" is employed in the present specification and claims to designate a straight or branched chain radical containing from 1 to 4 carbon atoms, such as, methyl, ethyl, propyl, isopropyl, butyl, isobutyl, secondary butyl and tertiary butyl.

The term "alkylamino" is employed in the present specification and claims to designate either a mono or dialkylamino radical wherein the alkyl portion of the radical is straight or branched and contains from 1 to 4 carbon atoms, such as methyl, ethyl, propyl, isopropyl, butyl, isobutyl, secondary butyl or tertiary butyl.

The term "halo" is employed in the present specification and claims to designate chloro, bromo, iodo or fluoro.

The aryl azines to be employed in the methods of the present invention are crystalline solids and are known compounds which can be obtained commercially or can be prepared by methods taught in the prior art literature.

Representative aryl azine which can be employed in the practice of the present invention include for example:
Benzaldehyde azine;
4-Tolualdehyde azine;
3-Tolualdehyde azine;
2,3-Dimethylaldehyde azine;
2,6-Dimethylbenzaldehyde azine;
2,4-Dimethylbenzaldehyde azine;
3,4-Dimethylbenzaldehyde azine;
2,6-Diethylbenzaldehyde azine;
3,5-Dibutylbenzaldehyde azine;
4-n-Propylbenzaldehyde azine;
4-Hydroxybenzaldehyde azine;
2-Hydroxybenzaldehyde azine;
3-Methoxybenzaldehyde azine;
4-Butoxybenzaldehyde azine;
3-Hydroxy-4-methoxybenzaldehyde azine;
4-Hydroxy-3-methoxybenzaldehyde azine;
4-Hydroxy-3-butoxybenzaldehyde azine;
3,4-Dimethoxybenzaldehyde azine;
2,4-Dimethoxybenzaldehyde azine;
2,4-Di-n-propoxybenzaldehyde azine;
4-Acetamidebenzaldehyde azine;
4-Dimethylaminobenzaldehyde azine;
4-Dimethylamino-2-ethoxybenzaldehyde azine;
4-Diethylaminobenzaldehyde azine;
3-Di-n-propylamino-4-methylbenzaldehyde azine;
3-Butylaminobenzaldehyde azine;
4-Fluorobenzaldehyde azine;
3-Chlorobenzaldehyde azine;
2-Bromobenzaldehyde azine; and
4-Iodobenzaldehyde azine.

The azine compounds employed in the practice of the present invention can be prepared by reacting two (2) molecular equivalents of an appropriately substituted benzaldehyde with one (1) molecular equivalent of hydrazine at temperatures of from about 22° C up to the reflux temperature of the mixture in the presence of a lower alkanol reaction medium and separating the thus formed azine product.

The practice of the present invention can be accomplished by the oral administration of an anthelmintically effective amount of the hereinabove set forth azine compounds. The administration of a therapeutic or prophylactic dose, or dose sufficient to control the nematodes without serious toxic effects on sheep, is essential and critical for the practice of the present invention. The exact dose to be administered may vary provided the required anthelmintic dosage is provided and is dependent upon the specific agent to be employed, as well as upon whether the administration is to be made in a single dose or in multiple doses over a period of several days. Where a single dose is employed, good results are obtained when the compounds are administered at a dosage of from about 5 to about 500 milligrams per kilogram of body weight (mg/kg) of the animal and preferably from about 25 to about 50 mg/kg of body weight.

The administration can be carried out by the feeding of the unmodified azine compounds. However, the present invention also embraces the employment of a liquid drench, powder, mash, pellet, bolus or other animal feed composition containing the azine derivatives. In such usage, the compounds may be modified with one or a plurality of additaments or innocuous ingestible adjuvants such as water, ethanol, skimmed milk, syrups, edible oils, surface active dispersing agents such as the liquid and solid dispersing or emulsifying agents; and edible solid carriers such as edible powders, mineral and vitamin supplements and commercial feeds, concentrates and supplements.

For direct oral administration to animals, both solid and liquid compositions containing from about 1 to about 95 percent by weight of the azine derivatives can be employed to supply the desired dosage. Where the compounds are provided as a constituent of the principal food ration, satisfactory results are obtained with food rations containing a minor but effective amount of the azine derivatives. The exact amount of the compound to be incorporated in the ration is dependent upon the food consumption and feeding habits of the animals concerned. For best results, it is preferred that the animal receive a dosage of from about 5 to about 500 mg/kg body weight per day. Where the compound is provided as a constituent of feed supplements, good results are obtained with supplements containing from 0.1 to 5 percent by weight of the azine derivatives. In compositions to be employed as concentrates, the active agents can be present in a concentration of from 2 to 98 percent by weight.

Liquid compositions containing the desired amount of the azine derivatives can be prepared by dissolving the compounds in an edible solvent or oil or by dispersing them in water with the aid of a suitable surface active dispersing agent such as an ionic or non-ionic emulsifying and dispersing agent. Suitable surface active agents include the glycerol and sorbitan esters of fatty acids and the polyoxyalkylene derivatives of fatty alcohols and sorbitan esters. The aqueous compositions can contain one or more water-immiscible oils as a solvent for the active agent. In such compositions, the water, oil and emulsifying agent constitute an aqueous emulsion carrier.

In the preparation of solid feed compositions, the azine compounds can be mechanically mixed with a finely divided edible solid such as flour or animal feed or a solid surface active dispersing agent such as finely divided bentonite, fuller's earth or attapulgite. These compositions can be administered in the form of bolus, capsule or tablet, or dispersed in an animal feed and such feed used to supply a part of the entire food ration. Alternatively the azine compounds can be dissolved in an organic solvent, the resulting mixture dispersed in an animal feed and the feed dried to remove the solvent. Also the compounds can be dispersed in an edible oil such as coconut oil, olive or peanut oil and the resulting mixture dispersed in the feed. There edible oil compositions can contain one of the aforementioned surface active agents.

The finished feed should contain protein, fat, fiber, carbohydrate, vitamins and minerals, each in an amount sufficient to meet the nutritional requirements of the animal for which the feed is intended. Most of these substances are present in naturally occurring feed materials, such as alfalfa hay or meal, cracked corn, whole oats, soybean oil meal, corn silage, ground corn cobs, wheat bran, and dried molasses. Bone meal, limestone, iodized salt and trace minerals are frequently added to supply the necessary minerals and urea to provide additional nitrogen.

As is well known to those skilled in the art, the types of diets are extremely variable depending upon the purpose, type of feeding operation, species, etc. Specific diets for various purposes are listed by Morrison in the Appendix of "Feeds and Feeding," The Morrison Publishing Company, Clinton, Iowa, 1959.

The following examples merely illustrate the invention and a manner by which it can be practiced and are not to be construed as limiting.

EXAMPLE 1

4-Actimidobenzaldehyde azine

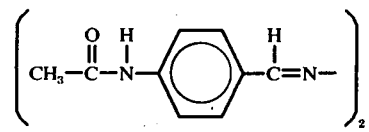

To a stirring solution of 65.2 grams (0.4 mole) of 4-acetamidobenzaldehyde in 500 cubic centimeters of ethanol was added 6.8 grams (0.2 mole) of 95 percent hydrazine. Upon this addition, the temperature of the reaction mixture increased (~5° C) and after 15 minutes, yellow crystals formed. The mixture was stirred at room temperature for one (1.0) hour and then at reflux for two (2.0) hours. The reaction mixture was cooled to 0° C and solids contained therein were recovered by filtration and dried to give 59.0 grams (91.5 percent of theoretical) of 4-acetamidobenzaldehyde azine, melting at 313°–315° C. The product was confirmed by infrared and nuclear magnetic resonance analysis (Compound I).

By following the hereinabove preparation procedure and employing the appropriate benzaldehyde, the following compounds are prepared.

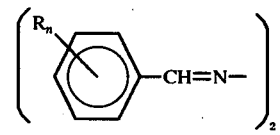

| Compound Number | R | Melting Point ° C |
|---|---|---|
| II | H | 91–93 |
| III | 4—CH$_3$ | 155–157 |
| IV | 4—OH | 278–279 |
| V | 3—CH$_3$O— | 74–76 |
| VI | 4—CH$_3$O—, 3—OH | 267–271 |
| VII | 3—CH$_3$O—, 4—OH | 175–177 |
| VIII | 3,4—(CH$_3$O—)$_2$ | 191–193 |
| IX | 4—(CH$_3$)$_2$N— | 263–4 |
| X | 4—(C$_2$H$_5$)$_2$N—, 2—C$_2$H$_5$O— | 224–225 |
| XI | 4—F | 180–182 |
| XII | 2,4—(CH$_3$O—)$_2$ | 198–201 |
| XIII | 4—(C$_2$H$_5$)$_2$N— | 188 |

EXAMPLE 2

A study was carried out to determine the anthelmintic efficacy of the hereinafter set forth compounds in the kill and control of Haemonchus in sheep.

Test Method:

Sheep which were of the approximate same age and which were naturally infected with the gastrointestinal nematode Haemonchus were selected at random to receive, by oral administration, in a single dose, a gelatin capsule containing a predetermined amount of one of the hereinafter set forth compounds.

The efficacy of the compounds was evaluated by comparing the average to two pretreatment counts of eggs per gram of feces and the average of two post-treatment counts of eggs per grams of feces. The pretreatment egg counts were made on days 1 and 2 prior to the administration of the compound and the average of the two counts was employed. The post-treatment egg counts were made on days 6 and 7 after administration of the compound and the average of the two counts was employed.

The results of this comparison, the compounds employed and the dosage administered are set forth below in Table I.

TABLE I

| Compound Number | Milligrams of Compound per Kilogram of Sheep body weight | Percent reduction in egg count per gram of feces |
| --- | --- | --- |
| I | 100 | 95 |
| II | 100 | 94 |
| III | 100 | 93 |
|  | 35 | 53 |
| IV | 100 | 98 |
|  | 100 | 94 |
|  | 50 | 92 |
|  | 25 | 100 |
| V | 100 | 93 |
|  | 100 | 86 |
| VI | 100 | 94 |
|  | 50 | 82 |
| VII | 100 | 93 |
|  | 35 | 74 |
| VIII | 100 | 100 |
| IX | 100 | 93 |
|  | 50 | 92 |
|  | 25 | 82 |
| X | 100 | 98 |
|  | 35 | 35 |
| XI | 100 | 74 |
|  | 100 | 37 |
| XII | 100 | 98 |
|  | 35 | 46 |
| XIII | 100 | 70 |
| Control | — | 0 |

What is claimed is:

1. A method for the control of Haemonchus in ruminant animals which comprises orally administering to said animals an anthelmintically effective amount of an aryl azine corresponding to the formula

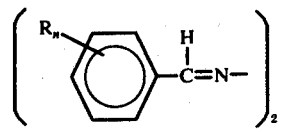

wherein R independently represents hydrogen, hydroxy, loweralkyl of 1 to 4 carbon atoms, loweralkoxy of 1 to 4 carbon atoms, alkylamino of 1 to 4 carbon atoms, acetamido or halo and n represents an integer of 1 or 2.

2. The method of claim 1 wherein the aryl azine is benzaldehyde azine.

3. The method of claim 1 wherein the aryl azine is 4-hydroxybenzaldehyde azine.

4. The method of claim 1 wherein the aryl azine is 4-dimethylaminobenzaldehyde azine.

5. The method of claim 1 wherein the aryl azine is 4-diethylaminobenzaldehyde azine.

6. The method of claim 1 wherein the aryl azine is 4-hydroxy-3-methoxybenzaldehyde azine.

7. The method of claim 1 wherein the aryl azine is 3-hydroxy-4-methoxybenzaldehyde azine.

8. The method of claim 1 wherein the aryl azine is 3-methoxybenzaldehyde azine.

9. The method of claim 1 wherein the aryl azine is 2,4-dimethoxybenzaldehyde azine.

10. The method of claim 1 wherein the aryl azine is 3,4-dimethoxybenzaldehyde azine.

11. The method of claim 1 wherein the aryl azine is 4-tolualdehyde azine.

12. The method of claim 1 wherein the aryl azine is 4-acetamidobenzaldehyde azine.

13. The method of claim 1 wherein the aryl azine is 4-diethylamino-2-ethoxybenzaldehyde azine.

14. The method of claim 1 wherein the aryl azine is 4-fluorobenzaldehyde azine.

15. An animal feed composition which comprises an animal feed and from 1–95 percent by weight of an aryl azine corresponding to the formula

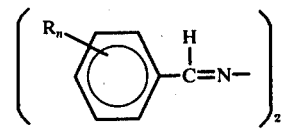

wherein R independently represents hydrogen, hydroxy, loweralkyl of 1 to 4 carbon atoms, loweralkoxy of 1 to 4 carbon atoms, alkylamino of 1 to 4 carbon atoms, acetamido or halo and n represents an integer of 1 or 2.

16. The composition of claim 15 wherein the aryl azine is benzaldehyde azine.

17. The composition of claim 15 wherein the aryl azine is 4-hydroxybenzaldehyde azine.

18. The composition of claim 15 wherein the aryl azine is 4-dimethylaminobenzaldehyde azine.

19. The composition of claim 15 wherein the aryl azine is 4-diethylaminobenzaldehyde azine.

20. The composition of claim 15 wherein the aryl azine is 4-hydroxy-3-methoxybenzaldehyde azine.

21. The composition of claim 15 wherein the aryl azine is 3-hydroxy-4-methoxybenzaldehyde azine.

22. The composition of claim 15 wherein the aryl azine is 3-methoxybenzaldehyde azine.

23. The composition of claim 15 wherein the aryl azine is 2,4-dimethoxybenzaldehyde azine.

24. The composition of claim 15 wherein the aryl azine is 3,4-dimethoxybenzaldehyde azine.

25. The composition of claim 15 wherein the aryl azine is 4-tolualdehyde azine.

26. The composition of claim 15 wherein the aryl azine is 4-acetamidobenzaldehyde azine.

27. The composition of claim 15 wherein the aryl azine is 4-diethylamino-2-ethoxybenzaldehyde azine.

28. The composition of claim 15 wherein the aryl azine is 4-fluorobenzaldehyde azine.

* * * * *

UNITED STATES PATENT AND TRADEMARK OFFICE
CERTIFICATE OF CORRECTION

PATENT NO. : 4,015,014
DATED : March 29, 1977
INVENTOR(S) : Robert D. Vatne et al.

It is certified that error appears in the above-identified patent and that said Letters Patent are hereby corrected as shown below:

Column 3, line 55, "there edi-" should read -- these edi- --.

Column 4, line 12, title of EXAMPLE 1, "4-Actimidobenzaldehyde azine" should read -- 4-Acetamidobenzaldehyde azine --.

Column 5, line 4, "average to" should read -- average of --.

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*